(12) United States Patent
Joyce et al.

(10) Patent No.: US 12,387,830 B2
(45) Date of Patent: Aug. 12, 2025

(54) MEDICAL ADHERENCE SYSTEM AND METHOD

(71) Applicants: HealthBeacon Limited, Dublin (IE); James Joyce, Needham, MA (US)

(72) Inventors: James Joyce, Needham, MA (US); Kieran Daly, Dublin (IE); Richard Shattock, Dublin (IE)

( * ) Notice: Subject to any disclaimer, the term of this patent is extended or adjusted under 35 U.S.C. 154(b) by 841 days.

(21) Appl. No.: 17/056,939

(22) PCT Filed: Jun. 26, 2019

(86) PCT No.: PCT/US2019/039269
§ 371 (c)(1),
(2) Date: Nov. 19, 2020

(87) PCT Pub. No.: WO2020/263245
PCT Pub. Date: Dec. 30, 2020

(65) Prior Publication Data
US 2021/0295975 A1    Sep. 23, 2021

(51) Int. Cl.
*A61B 50/36*   (2016.01)
*A61M 5/50*    (2006.01)
(Continued)

(52) U.S. Cl.
CPC ............ *G16H 20/17* (2018.01); *A61B 50/36* (2016.02); *A61B 50/362* (2016.02); *A61M 5/5086* (2013.01); *G06N 5/04* (2013.01); *G06N 20/00* (2019.01); *G06Q 10/30* (2013.01); *G09B 9/00* (2013.01); *G16H 10/60* (2018.01);
(Continued)

(58) Field of Classification Search
CPC ........ G16H 20/17; G16H 10/60; G16H 40/40; G16H 40/67; G16H 15/00; G16H 40/20; G16H 70/40; G16H 20/10; A61B 50/36; A61B 50/362; A61B 50/3001; A61M 5/5086; A61M 2205/3553; A61M 2205/3584; A61M 2205/50; A61M 2205/52; G06N 5/04; G06N 20/00; G06Q 10/30; G09B 9/00; H04M 1/72409;
(Continued)

(56) References Cited

U.S. PATENT DOCUMENTS

| 10,074,059 B1 | 9/2018 | Albro |
| 2007/0080223 A1* | 4/2007 | Japuntich ............. A61B 50/362 374/E1.004 |

(Continued)

FOREIGN PATENT DOCUMENTS

| KR | 10-2013-0137968 A | 12/2013 | |
| WO | WO-2016040376 A1 * | 3/2016 | ......... G06F 19/3456 |
| WO | 2017035474 A1 | 3/2017 | |

OTHER PUBLICATIONS

International Search Report and Written Opinion received in International Application No. PCT/US2019/039269, mailed on Sep. 18, 2019, 46 Pages.

*Primary Examiner* — Sheetal R Paulson
(74) *Attorney, Agent, or Firm* — Conley Rose, P.C.; Brooks W Taylor

(57) ABSTRACT

A system includes a smartphone, a connected sharps container, the connected sharps container communicatively linked to the smartphone, and a web server, the web server communicatively linked to the smartphone and to the connected sharps container.

14 Claims, 2 Drawing Sheets

(51) Int. Cl.
| | |
|---|---|
| *G06N 5/04* | (2023.01) |
| *G06N 20/00* | (2019.01) |
| *G06Q 10/30* | (2023.01) |
| *G09B 9/00* | (2006.01) |
| *G16H 10/60* | (2018.01) |
| *G16H 20/17* | (2018.01) |
| *G16H 40/40* | (2018.01) |
| *G16H 40/67* | (2018.01) |
| *H04M 1/72409* | (2021.01) |
| *A61J 7/04* | (2006.01) |
| *G06K 7/14* | (2006.01) |
| *G16H 15/00* | (2018.01) |
| *G16H 40/20* | (2018.01) |
| *G16H 70/40* | (2018.01) |

(52) U.S. Cl.
CPC ............ *G16H 40/40* (2018.01); *G16H 40/67* (2018.01); *H04M 1/72409* (2021.01); *A61J 7/0481* (2013.01); *A61J 2200/30* (2013.01); *A61M 2205/3553* (2013.01); *A61M 2205/3584* (2013.01); *A61M 2205/50* (2013.01); *A61M 2205/52* (2013.01); *G06K 7/1417* (2013.01); *G16H 15/00* (2018.01); *G16H 40/20* (2018.01); *G16H 70/40* (2018.01)

(58) Field of Classification Search
CPC ... G06K 7/1417; A61J 2200/70; A61J 7/0418; A61J 7/0436; Y02W 90/00
See application file for complete search history.

(56) References Cited

U.S. PATENT DOCUMENTS

| | | | |
|---|---|---|---|
| 2013/0261794 | A1 | 10/2013 | Fauci |
| 2014/0374294 | A1* | 12/2014 | Joyce ..................... A61B 50/36 206/363 |
| 2019/0209433 | A1* | 7/2019 | Fateh ........................ A61J 1/16 |
| 2021/0158926 | A1* | 5/2021 | Gylleby ................. A61B 50/24 |
| 2021/0217156 | A1* | 7/2021 | Balachandran ........ G06V 20/00 |
| 2021/0295975 | A1* | 9/2021 | Joyce ..................... G09B 9/00 |

* cited by examiner

MEDICAL ADHERENCE SYSTEM AND METHOD

CROSS-REFERENCE TO RELATED APPLICATIONS

This present application claims priority as a national stage application submitted under 35 U.S.C. 371 from PCT/US2019/039269 filed Jun. 26, 2019, the entire contents of which are hereby incorporated by reference herein.

BACKGROUND OF THE INVENTION

The present invention relates generally to an administration of medication, and more particularly to a medical adherence system and method.

Medications, including prescription and over-the-counter pharmaceuticals, as well as vitamins and other dietary supplements, form a mainstay of health care, maintenance, and disease management and prevention. Typically a medication is given in repeated doses spread out over time so as to sustain desired levels of active ingredients in the patient's body. Any substantial deviation from the recommended timing, such as missing a dose or "doubling up" on doses, may decrease a medication's effectiveness or cause outright harm to the patient.

What is needed is a system and method to ensure that medications are being taken on the prescribed schedule.

BRIEF SUMMARY OF THE INVENTION

The following presents a simplified summary of the innovation in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

In general, in one aspect, the invention features a system including a smartphone, a connected sharps container, the connected sharps container communicatively linked to the smartphone, and a web server, the web server communicatively linked to the smartphone and to the connected sharps container.

In another aspect, the invention features a connected sharps container including an input/output device, a memory, a processor, a wireless receiver/transmitter, a sensor, a door, and a collection chamber.

In still another aspect, the invention features a smartphone including a processor, a memory, the memory comprising at least an operating system and a medical adherence app, and an input/output device, the medical adherence app configured to wirelessly communicate with a connected sharps container.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

These and other features, aspects, and advantages of the present invention will become better understood with reference to the following description, appended claims, and accompanying drawings where:

DETAILED DESCRIPTION OF THE INVENTION

Figure 1:
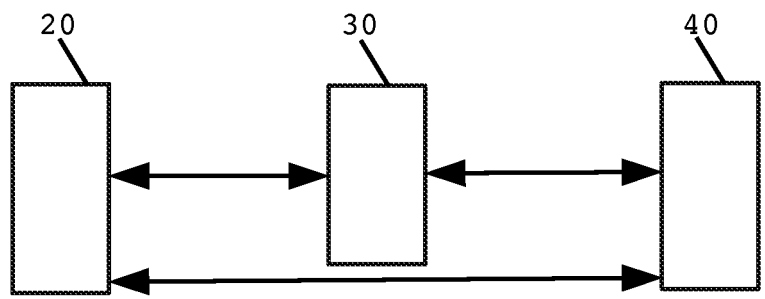
FIG. 1 is a block diagram of an exemplary medical adherence system.

The subject innovation is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

The present invention relates to a packaging device and use-monitoring system for items intended to be dispensed over a period of time or on a particular schedule, such as prescription medications. The present invention can be directed towards patients who would benefit from easier access to their medication. The medicine management system may be connected to external networks and/or system and thus serve as an adherence management system to assist with tracking a patient's medication schedule and adherence to such schedule.

As shown in FIG. 1, an exemplary medical adherence system 10 includes a smartphone 20, a connected sharps container 30 and a web server 40. In one embodiment, the smartphone 20 is communicatively linked to the connected sharps container 30 and the web server 40 and the connected sharps container 30 is communicatively linked to the web server 40. In such an arrangement, each of the components 20, 30, 40 may communicate with each other. In one implementation, the communication links between the smartphone 20, the connected sharps container 30 and the web server 40 are wireless.

Figure 2:
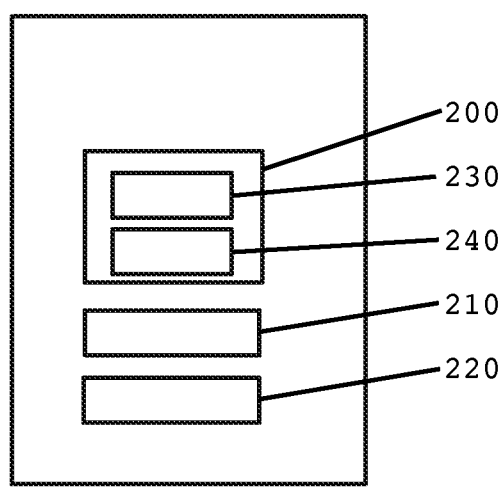
FIG. 2 is a block diagram of a smart phone.

As shown in FIG. 2, the smartphone 20 includes at least a memory 200, a processor 210 and an input/output device 220, such as a display. Memory 200 includes an operating system 230, such as iOS® or Android®, and a medical adherence app 240.

Figure 3:
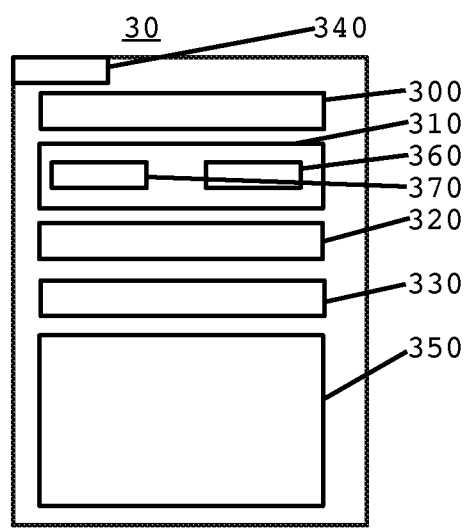
FIG. 3 is a block diagram of a connected sharps container.

As shown in FIG. 3, the connected sharps container 30 includes at least an input/output device 300, a memory 310, a processor 320, a wireless receiver/transmitter 325, a sensor 330, a door 340 and a collection chamber 350. The memory 310 includes at least an operating system 360, such as Android®, and a medical adherence module 370. It is simplest operation, an injectable device (not shown), for example, deposited through the door 340, is detected by the sensor 330 as an event prior to dropping into the collection chamber 350. Moreover, the input/output device 300 enables a user to program the connected sharps container 30 with a patient's injectable disposal schedule and records when an injectable device is deposited into the connected sharps container 30.

The medical adherence app 240 on the smartphone 20 presents a user interface that enables a user to interact with the connected sharps container 30. More specifically, the medical adherence app 240 user interface provides a digital interface to the user (i.e., patient) with information about their connected sharps container 30 and enables them to control and set parameters and functionality of the connected sharps container 30.

The medical adherence app user interface provides the user an ability to input information and change preferences that can be linked to their medication disposal schedule. This updates the connected sharps container 30. For example, the medical adherence app 240 can display a user dashboard on the user interface that enables a patient to self-report if they have followed their prescription schedule but were unable to deposit it into the bin, such as when they are away on vacation.

The medical adherence app 240 can prompt the patient in the user interface when to take and deposit their used medication.

The medical adherence app 240 is updated when a patient deposits a used injectable medication into the connected sharps container 30, providing details on their next disposal event.

The medical adherence app 240 is configured to display a range of outputs, including a patient's disposal score, a number of injections they have deposited and a number of injections they were scheduled to deposit. The medical adherence app 240 is also configured to indicate the next scheduled disposal time and provide a countdown to this date and provide notifications as per preferences set by the patient.

The medical adherence app 240 can be configured to display a site at which the patient previously injected their medication and where they are due to administer their next injection.

The medical adherence app 240 is configured to utilize augmented reality training modules to educate the user and improve performance. In addition, predictive algorithms and machine learning with data gathered from the connected sharps container 30 can help improve user experiences and use by providing appropriate delivered content and notifications to prompt timely disposal events.

The data collected by the connected sharps container 30 and the medical adherence app 240 is configured to summarized information for review by a Healthcare professional, caregiver or family member. For example, the medical adherence app 240 can execute a nurse application that provides a caregiver with details about their patient's disposal/user application engagement and allows for notifications, reminders for specific visits or follow ups that are scheduled or if they are struggling with the disposal of their medication. In addition, the patient can directly message a nurse or request additional services, such as waste management, through the application dashboard of the medical adherence app 240. Similarly, the medical adherence app 240 can execute a physician application to provide a doctor with details on their specific patients and if their disposal history is correlating with their medication prescription schedule.

In one specific embodiment, the medical adherence app 240 includes a Digital Augmented Reality Intervention Nurse Advisor ("DARINA") For Connected Sharps container. Here, the connected sharps container 30 or patient information material contains an AR Code or QR code, which is scanned by the patient with their smartphone 20. In response, a DARINA pops up and provides training on the use of the connected sharps container 30 for the selected medication. The projected nurse can assist and communicate at regular milestone intervals and intervene at appropriate times, answers Frequently Asked Questions (FAQs) and provide reminders depending on the patient's interaction (or non-interaction) with the connected sharps container.

In one embodiment, the medical adherence app 240 includes a predictive algorithm process (continually analyzing the user's engagement and previous engagement with the connected sharps container) configured to determine if the patient is likely to struggle with their prescription schedule and provide the necessary alerting infrastructure through DARINA to assist with user compliance. The predictive algorithm process can sense and collect info as machine learning and Artificial Intelligence (AI) allows informed medical treatment through the DARINA system.

The medical adherence app 240 can solicit input from a user and sent to the web server 40 where the received input can be analyzed in conjunction with data received by multiple users to, for example, improve technical support.

The medical adherence system 10 enables unique patient care. For example, the connected sharps container 30 can contain information about a patient's medicine and the connected sharps container 30 may be provided with a unique barcode, AR or QR code, that once scanned by a scanner function on the smart phone 20 populates the medical adherence app 240 with the most up to date information about the medication that the patient is taking.

The medical adherence app 240 can generate a disposal adherence score, i.e., a score representing details of how many injections that a patient has disposed of in a certain timeframe, classified as "on-time," "missed" or "late," for example. In one implementation, the disposal adherence score is presented as a percentage score.

When a patient is prescribed a medication, a physician recommends a frequency to take the medication. This frequency is programmed into the connected sharps container 30 and correlates closely with when the patient disposes of their medication. Sometimes the schedule may not suit the patient due to general day to day or work/life activities. As such, the medical adherence app 240 allows the patient change this schedule to better suit their needs. As patient support providers currently perform this task and manually update the process following a phone call from the patient, the medical adherence app 240 provides increased flexibility and ease of use for a patient managing a chronic disease.

When a user first has their connected sharps container 30 programmed, it provides times to receive text reminders to remind them when to dispose of their medication. The user may want to change these preferences to better suit their lifestyle. Instead of contacting their patient support provider, the patient can set these using the medical adherence app 240. These reminders can include one or a combination of text reminders, emails, audio, visual lighting, phone calls or visits and can also set multiple reminders on disposal or medication events or if their connected sharps container 30 is unplugged or the battery requires changing (e.g., in the case of a battery powered sharps bin container 30 or connected sharps bin lid system).

The medical adherence app 240 includes an appointment scheduling feature. A patient can use the appointment scheduling feature to request a nurse visit or doctor's appointment. The appointment scheduling feature has the ability to allow patients to order new medication prescription refills and can be customized to provide medication/customer branding.

The medical adherence app 240 enables a patient to record a self-report a disposal event. More specifically, the patient has the ability to provide details into the medical adherence app 240 (such as date and time) of when they administered their medication if they were not near their connected sharps container 30, such as when on vacation.

Alternatively, the medical adherence app 240 provides an ability for the patient to submit an image of their injectable device after they have administered. This uploaded image can then be reconciled to the disposal event expected into the connected sharps container 30.

The medical adherence app 240 enables a patient to self-report other events, such as in cases where a patient may need to take an extra injection such as when they experience a flare up or in an emergency, they may need to reflect this extra disposal event and the details within the application dashboard so that the connected sharps container schedule can be updated. Depending on the patient's disease they may sometimes suffer attacks which may require documentation. These can be updated to the calendar and may send notifications to caregivers to notify of such events.

In some cases, a patient may need to take an emergency dose. This dose can be identified as not in keeping with their regular maintenance dose as it may be out-of-sync with the expected prescription & disposal calendar. As such the medical adherence system 10 can be set-up to send alert notifications to caregivers or emergency responders with key information to rapidly assist, including location.

Often patients may become ill and require that their disposal schedule is paused while they overcome their illness as recommended by their physician. In this instance, they would typically contact a helpline to request the pausing of this treatment schedule as it would impact negatively on their disposal adherence score. The medical adherence app 240 allows the patient to pause their treatment. An injection expected within that time frame would not impact on their score. A timeframe can be set, one week for example, after which, the treatment would reactivate. Or the patient can simply select on/off when they wish to pause or recommence.

In one embodiment, the medical adherence system can include a second smartphone (not shown) belonging to a healthcare professional or family member. The second smartphone may include its own medical adherence app that mirrors the medical adherence app 240 of the patient and provides access to notifications in cases where they need to be aware that the patient is taking their medication and therefore disposing of their injections in a timely manner.

The medical adherence app 240 includes a calendar function which forward projects a patient's disposal calendar and allows the patient to edit these if required or to add or to set additional notification events, reminders or appointments. If a nurse visit or doctor visit is requested through the medical adherence app 240 or a report is sent to the doctor, this information is recorded automatically to the calendar.

In one embodiment, the connected sharps container 30 includes an external electronic unit that has an internal disposable container that can be replaced. When the container becomes full of used sharps needles or other injectable devices they are swapped. As the sharp's container records the disposal of each needle, the connected sharps container 30 knows when the bin is becoming full based on a total capacity of the unit and a size of the injectable that has been deposited into it. This allows service providers the ability to monitor when bins require to be exchanged and can schedule accordingly. Patient's also have the option of requesting a new bin to be delivered and their old bin exchanged through the medical adherence app 240.

In summary, medical adherence system 10 provides tailored control of a patient's connected sharps container 30 by giving the patient the ability to manage, change and update key parameters of the connected sharps container 30. This reduces a need to reach out to their nurse, or support line to have these details updated on the system. The medical adherence app 240 provides a powerful tool for patient self-management of their disease and allows the patient to remain in control of their medication schedule, yet keep their health care professionals and caregiver teams in sync with their disposal and medication history. This reduces time, cost and provides positive reinforcement to a patient that they are controlling their illness effectively.

It would be appreciated by those skilled in the art that various changes and modifications can be made to the illustrated embodiments without departing from the spirit of the present invention. All such modifications and changes are intended to be within the scope of the present invention except as limited by the scope of the appended claims.

What is claimed:

1. A system comprising:
   a smartphone;
   a connected sharps container comprising an external electronic unit, an internal, replaceable and disposable collection chamber, and an opening to the replaceable and disposable collection chamber, the opening including at least a sensor configured to sense and record an item passing through the opening prior to dropping into the replaceable and disposable collection chamber, the connected sharps container communicatively linked to the smartphone and configured to send a message to the smartphone in response to the sensor sensing the item passing through the opening into the replaceable and disposable collection chamber; and
   a web server, the web server communicatively linked to the smartphone and to the connected sharps container,
   wherein a medical adherence app residing in the smartphone is configured to:
   provide a digital interface to a user with information about the connected sharps container, and
   enable the user to control and set parameters and functionality of the connected sharps container.

2. The system of claim 1 wherein the smartphone comprises:
   a processor;
   a memory, the memory comprising at least an operating system and the medical adherence app; and
   an input/output device.

3. The system of claim 2 wherein the connected sharps container comprises:
   a communication device configured to communicate with the medical adherence app and the web server;
   a memory;
   a processor; and
   an input/output device.

4. The system of claim 3 wherein the input/output device of the connected sharps container is configured to receive instructions and store the instructions in the memory of the connected sharps container.

5. The system of claim 4 wherein the instructions are a patient's injectable disposal schedule.

6. The system of claim 1 wherein the medical adherence app comprises predictive algorithms and machine learning with data gathered from the connected sharps container that helps improve the user's experience and use by providing appropriate delivered content and notifications to prompt timely disposal events.

7. The system of claim 1 wherein the medical adherence app is further configured to prompt the user via the user interface when to take and deposit their used medication.

8. A connected sharps container comprising:
   an external electronic unit;

an input/output device;
a memory;
a processor;
a wireless receiver/transmitter;
a sensor;
a door; and
an internal, replaceable and disposable collection chamber,
wherein the sensor is configured to detect an injectable device deposited through the door prior to the injectable device dropping into the replaceable and disposable collection chamber and record the detection as an event.

9. The connected sharps container of claim 8 wherein the memory comprises:
an operating system; and
a medical adherence module.

10. The connected sharps container of claim 9 wherein the input/output device enables a user to program the connected sharps container with an injectable disposal schedule.

11. The connected sharps container of claim 10 wherein the medical adherence module causes an injection reminder to be wirelessly transmitted to a smartphone of the user.

12. The connected sharps container of claim 9 wherein the medical adherence module is configured to wirelessly transmit the event to a web server.

13. A smartphone comprising:
a processor;
a memory, the memory comprising at least an operating system and a medical adherence app; and
an input/output device;
the medical adherence app configured to store a schedule for disposal of patient injectable devices into a connected sharps container and to communicate wirelessly with the connected sharps container.

14. The smartphone of claim 13, wherein the medical adherence app is further configured to:
receive disposal notifications from the connected sharps container;
receive usage and reminder notifications; and
communicate with a healthcare professional.

* * * * *